(12) United States Patent
Cohen et al.

(10) Patent No.: US 8,571,804 B2
(45) Date of Patent: Oct. 29, 2013

(54) DISEASE TREATMENT BY PREDICTING DRUG ASSOCIATION

(75) Inventors: Daniel Cohen, Le Vesinet (FR); Ilya Chumakov, Vaux le Penil (FR)

(73) Assignee: Pharnext, Paris (FR)

( * ) Notice: Subject to any disclaimer, the term of this patent is extended or adjusted under 35 U.S.C. 154(b) by 19 days.

(21) Appl. No.: 12/744,363

(22) PCT Filed: Nov. 28, 2008

(86) PCT No.: PCT/EP2008/066457
§ 371 (c)(1),
(2), (4) Date: May 24, 2010

(87) PCT Pub. No.: WO2009/068659
PCT Pub. Date: Jun. 4, 2009

(65) Prior Publication Data
US 2010/0234236 A1 Sep. 16, 2010

(30) Foreign Application Priority Data
Nov. 30, 2007 (EP) ..................................... 07301609

(51) Int. Cl.
*G06F 19/00* (2011.01)
*G06F 19/12* (2011.01)
*G06F 17/10* (2006.01)

(52) U.S. Cl.
USPC .............................................. 702/19; 703/11

(58) Field of Classification Search
None
See application file for complete search history.

(56) References Cited

U.S. PATENT DOCUMENTS

| 2005/0060305 A1 * | 3/2005 | Hopkins et al. .................. 707/3 |
| 2005/0187290 A1 | 8/2005 | Fontes et al. |
| 2007/0269834 A1 | 11/2007 | Shapiro |

FOREIGN PATENT DOCUMENTS

WO  WO 2004/006911  1/2004

OTHER PUBLICATIONS

O'Connor et al. (Nature Reviews (2005) vol. 4, pp. 1005-1014).*
Li et al. (Genome Informatics (2006) vol. 17, pp. 239-247).*
Hopkins et al. (Annual Reports in Medicinal Chemistry (2005) vol. 40, pp. 349-358).*
Loging et al. Nature Mar. 2007; vol. 6:220-230).*
Borisy et al. (PNAS (2003) vol. 100, No. 13, pp. 7977-7982).*
Ashburn, T. T. et at "Drug Repositioning: Identifying and Developing New Uses for Existing Drugs", *Nature Reviews Drug Discovery*, Aug. 2004, pp. 673-683, vol. 3, XP-002469384.
Bisson, W. H. et al. "Discovery of antiandrogen activity of nonsteroidal scaffolds of marketed drugs", *PNAS*, Jul. 17, 2007, pp. 11927-11932, vol. 104, No. 29, XP-002469382.
Dingemanse, J. et al. "Integrated Pharmacokinetics and Pharmacodynamics in Drug Development" *Clinical Pharmacokinetics*, Jan. 1, 2007, pp. 713-737, vol. 46, No. 9, XP-008088703.
Michelson, S. et al. "In silico prediction of clinical efficacy" *Current Opinion in Biotechnology*, 2006, pp. 666-670, vol. 17, No. 6, XP-005779253.
Tartaglia, L. A. "Complementary new approaches enable repositioning of failed drug candidates", *Expert Opin. Investig. Drugs*, 2006, pp. 1295-1298, vol. 15, No. 11, XP-002469383.

* cited by examiner

*Primary Examiner* — Lori A. Clow
(74) *Attorney, Agent, or Firm* — Saliwanchik, Lloyd & Eisenschenk

(57) ABSTRACT

The present invention relates to methods for drug repositioning. More particularly, this invention relates to methods for selecting approved drugs or combinations of approved drugs for use in new therapeutic indications. This approach is situated in a cross section between drug repositioning and disease treatment by combinations of drugs with additive or synergistic action. The invention also allows to define drugs or drug combinations for treating the unmet medical need in diseases neglected by majority of Pharma companies, such as orphan diseases.

8 Claims, No Drawings

DISEASE TREATMENT BY PREDICTING DRUG ASSOCIATION

CROSS-REFERENCE TO RELATED APPLICATION

This application is the U.S. national stage application of International Patent Application. No. PCT/EP2008/066457, filed Nov. 28, 2008, the disclosure of which is hereby incorporated by reference in its entirety, including all figures, tables and amino acid or nucleic acid sequences.

The present invention relates to methods for drug repositioning. More particularly, this invention relates to methods for selecting approved drugs or combinations of approved drugs for use in new therapeutic indications. This approach is situated in a cross section between drug repositioning and disease treatment by combinations of drugs with additive or synergistic action. The invention also allows to define drugs or drug combinations for treating the unmet medical need in diseases neglected by majority of Pharma companies, such as orphan diseases.

Many strategies are being implemented by pharmaceutical companies to identify new drugs. These include screening of combinatorial libraries of chemical pharmacophores and high throughput screening of combinatorial libraries of molecules to determine their activity for a selected validated target or disease relevant phenotypical endpoint. However, these approaches have not allowed so far the identification with a sufficient degree of success of safe and efficient drugs.

Michelson et al (Curr Opin Biotech 17 (2006) 666) relates to a method of developing new therapeutic molecules for selected diseases. According to this method, a pharmacokinetic model of a drug is produced to identify a responder sub-population.

Other approaches are based on drug repositioning, that has been used to find the new therapeutic indications for approved drugs (Ashburn and Thor, 2004). Drug repositioning is particularly attractive for rare orphan diseases for which resources are limited (Rustin et al 1999, De Leersnyder et al 2003, Mercuri et al 2004).

In this regard, Bisson et al (PNAS 104 (2007) 11927) relates to a method of <<drug repurposing>> for the development of novel non-steroid antagonists of the human androgen receptor. In this method, drugs known to have, as a secondary target, the human androgen receptor, are identified, modified to avoid any action on their primary target, and tested. This approach thus requires the identification drugs having several targets. This method is also based on the drug, not on the disease model.

Therefore, it appears that the existing strategies used in drug repositioning contain various drawbacks which limit their effectiveness and ability to generate efficient drugs or drug combinations. These drawbacks are mostly related to the fact that drug repositioning has been drug oriented (to find new therapeutic area for the old drug) rather than disease oriented (to find new therapies based on old, approved drugs).

The present invention now discloses a novel method of drug repositioning, which allows the identification of clinically validated drugs and/or drug combinations for treating targeted diseases. By following the present method, the inventors have been successful in rapidly identifying approved drugs for treating various selected diseases, showing the efficacy and biological relevance of the proposed drug screening.

More specifically, the present invention relates to a method of identifying drugs, comprising the steps of:

a. selecting a disease to be treated;
b. building a dynamic model of the disease;
c. in silico screening of drugs approved for other diseases that targets pathways implicated in the model; and
d. testing drugs selected in c., either alone or in combination(s), in a biological model of the disease, to identify biologically active (approved) drugs or combinations thereof. These drugs or combinations are candidates for the treatment of said selected disease.

A further object of the invention is a method of producing a drug, the method comprising 1) identifying a drug using the above-described method and 2) producing the drug, preferably in a pharmaceutically acceptable form.

One important advantage of the invention is that it is a disease-oriented drug screening. Indeed, the method first comprises a step of building a specific dynamic model of the selected disease, which then allows a precise and relevant screening of approved drugs suitable for the treatment of this disease.

Disease Selection

The invention may be used to define suitable drug treatment for any type of disease, such a neurologic disorders, psychiatric disorders, cancers, autoimmune diseases, cardiovascular diseases, lipid-metabolism diseases, etc. Specific examples of such diseases include neurodegenerative disorders, neuropathies and cancers.

In a particular embodiment, the invention is used to define appropriate drugs or drug combinations for treating rare, orphan diseases and common diseases with unmet therapeutic need, such as neuropathies, diabetic and drug-induced neuropathies, amyotrophic lateral sclerosis (ALS), stroke, Parkinson's disease, Alzheimer diseases and other dementia, schizophrenia, bipolar disorder, major depression, etc.

In a more particular embodiment, the invention is used to define suitable drug treatment for the CMT disease which is an orphan genetic peripheral poly neuropathy.

Orphan disease means either a rare disease which has a very low prevalence in the population (approximately 5 per 10,000 or less than 200000 for the country like USA) or a common disease that has been ignored (such as tuberculosis, cholera, typhoid, and malaria) because it is far more prevalent in developing countries than in the developed world. These diseases are largely neglected by majority of Pharmaceutical companies.

The present invention is particularly suitable to define drug treatment for multi-factorial diseases or diseases manifesting clinical heterogeneity due to various modulator genes acting on implicated pathways, even if the disease has a monogenic origin. Indeed, modulating only one protein activity from these pathways can only have a marginal effect due to multiple natural regulatory events. Therefore, even if a disease is known to be mono-factorial, it has to be considered as multi-factorial from a therapeutic point of view. In this case, combining several drugs will be then more effective, particularly if synergic phenomenon can be observed.

Building a Dynamic Model of the Disease

The purpose of building a dynamic model of the disease is to define the most relevant mechanisms or cell targets by which the disease may be influenced or corrected. This expert approach represents an essential step of the method, resulting in the provision of a list of several drugs, including generics, approved for other diseases that we can be tested, either alone or in combinations, in biological models.

Our data mining rationale is based on the assumption that even for treating a disease triggered by mutations in a single gene, we should target and restore the function of underlying pathways rather than to try to restore the causal gene itself. This approach consists in using rational compensatory treatments addressing cellular pathways affected by the mutant gene(s) and which could slow down the progression of pathological conditions. According to this paradigm, disease-associated pathway or a group of pathways rather than isolated gene(s) are recognized as targets for drug development. This approach allows:

To define new therapeutic indications for known drugs, when they are able to modulate activity of disease-relevant pathways, and thus to find a way for modulating the activity of key disease-related genes for which drugs do not exist;

To treat several different pathways concurrently with the aim to achieve an additive effect by combining several drugs;

To perform this combinational treatment with lower doses of the selected drugs thus decreasing their risks of side effects.

The first step for building a dynamic model of the disease comprises compiling available published experimental data describing disease phenotype at genomic, biochemical, cellular and organism levels. Whole genome association data available now for many diseases represent most valuable resource for such analysis. Mining of these data can then be complemented by relevant information extracted from public or private databases such as Thomson Pharma, FDA, Drug-Bank or Ingenuity.

Based on these publicly available data describing molecular mechanisms and pathological manifestations of the disease, all available information is linked into logically supported pathways involved in disease genesis and progression.

With the help of population genetics the disturbed pathways can be identified by a global statistical analysis of all SNP (single nucleotide polymorphism) of a pathway implicated in the model of the disease. First of all we calculate statistical evidence not for individual SNP markers, but for group of markers located in the regions of genes and their flanks This approach permitted to effectively control the number of false positive results. The variation of SNP allelic differences from all the genes from single given pathway that represents the accumulated combination of multiple changes that are rarely significant when considered alone were used in order to demonstrate the association of pathways with disease phenotype. Indeed, the global statistical difference between a "normal" pathway and a "pathological" pathway is becoming significant when we consider the combination of all slightly significant SNP frequency differences. As an example to illustrate the rationale for considering the combination of a whole pathway linked variables, a protein could have a normal expression level (i.e. the same in patient and controls) but, in the context of a whole disturbed pathway, its "relative" effective amount could be in fact abnormal and this apparently normal expression level could contribute to pathology.

Pathways pertinent for therapeutic action are then determined by comparing the statistics of combination of SNP's from the different genes involved in each of them. By the same approach the pathological pathways are deduced from differential expression analysis of RNA using cytologically matched control and disease samples and performing statistical analysis in considering pathways rather than single expressed genes. These data are cross-compared with genetic association statistics and being used to further validate emerging pathogenic pathways. Other methods of gene product identification such as proteomic, metabolomic etc. are equally suitable for identification of disease pathways and being used to merge in final statistical score to prioritize further steps.

For this goal, multivariate statistical methods are used such as analysis of complex haplotypes, regression models, clustering, pattern recognition etc. Our approach consists in testing all available data on whole pathway association rather than single molecular marker association (considering allelic or genotypic frequency for genes or quantity differences for RNA, Proteins or Metabolites).

By constructing initial biological hypothesis disclosing the roles of particular cellular signalling pathways in establishment of the disease phenotype, few functional cellular modules can then be underlined as targets for relevant therapeutic interventions. These modules can be, for instance, the regulation of gene expression, the maturation/degradation of a protein or the control of a specific cell type proliferation. Thus, based on this dynamic model of the disease, a proposition of combinatorial treatments aiming to revert this disease status can be formulated.

Schematically our approach consists not in the treatment of single markers, but rather in statistic analysis of groups of genes in pathways, validation of these results in another data set (e.g. transcriptome data) and organization of emerging pathways in hierarchical model for in silico screening for potential small molecule regulators.

In Silico Screening of Drugs that Target the Dynamic Model

Once a model of the disease has been established, a virtual, i.e., in silico, typically computer assisted, screen of drugs that affect the model can be accomplished.

In a preferred embodiment, the screening is made from a library of approved drugs, including generics. Indeed, protein pleiotropy, meaning that a single protein may have several different functions, could explain in part drug toxicity even for very specific molecules, but also could lead to the possibility of re-using the same molecule for multiple different indications.

Such libraries are available, such as LOPAC$^{1280}$™ (Sigma Aldrich, See Worldwide Website: sigmaaldrich.com/Area_of_Interest/Chemistry/Drug_Discovery/Validation_Libraries/Lopac1280home.html), the UWCCC Small Molecule Screening Facility of the university of Wisconsin (See Worldwide Website: hts.wisc.edu/Libraries.htm), the Spectrum Collection, the US Drug Collection or the NINDS Collection of MicroSource Discovery Systems, Inc. (See Worldwide Website: msdiscovery.com).

Typically, the screening comprises the selection of drugs which are known to interact with a target or pathway contained in the dynamic model of the disease.

In a preferred embodiment, the screening is made on drugs targeting functional cellular modules identified as relevant for therapeutic interventions during the preceding step.

In order to define possible combinations and actions, hypotheses are assumed on the use and the effect of such selected drugs based on their known activities, and on possible synergy effects according to the respective targets of these drugs.

The performance of these steps readily resulted in a first list of generic drugs and combinations thereof, to be tested in biological models of the disease.

Testing in Biological Models

The testing is typically performed in a suitable in vitro (e.g., cellular) and/or in vivo (e.g. transgenic animal) model of the disease. In vitro testing is used for initial evaluation of the potential efficiency of selected approved drugs, e.g. to modulate the expression levels of a relevant target of the disease model. This may be tested by a number of approaches known per se in the art, using appropriate cell culture and reading systems.

Drugs that show activity individually are tested as combinations, at different concentrations, in order to find synergistic effects. The combination of drugs produces a matrix of multiple mixtures, containing both drugs at a variety of concentrations and ratios. Analysis of the results obtained with the combinations and individually is performed with computer programs such as CalcuSyn software. This program permits to discriminate between the combinations providing equivalent (additive), poorer (antagonism) or supra-additive (synergy) effect.

In one embodiment, each test compound is contacted, either alone or in combination, with a cell culture expressing the target of interest, and the effect of such contacting is measured.

In another embodiment, the study of valuable test compounds is complemented by experiments with micro-arrays (Vigo 2005; Shworer 2003). These experiments may also help to reveal new molecular pathways that may be targeted with drugs.

The method of the invention can also comprises a further step to confirm the in vitro study which consists in re-testing the successful drugs and combinations in a specific "pathological environment", such as cells isolated from a transgenic animal model of the selected disease. This step insures that the drugs active in normal cells are still operational in cells from the disease model.

Compounds or combinations of compounds which modulate by more than 10%, 20% or preferably 50% expression of the target are selected and can be used for further in vivo tests using animal model of the disease.

In a particular embodiment, further confirmative in vivo studies may be performed to test the drug or drug combination efficacy at organism level, to determine the best administration way and, if necessary, to perform initial pharmacokinetic analysis for the resulting mixtures of drugs. All these steps are fulfilled in order to obtain validated repositioned drugs or combinations.

The animal model for in vivo studies can be already available or created for this test according to techniques well-known by a person skilled in the art.

In one embodiment, each selected test compound is administered, either alone or in combination, to a transgenic animal model of the selected disease and the biological effect is measured.

In a preferred embodiment, the biological effect is the modulation of the expression of a target gene.

Depending on the type of treatment different statistical tests are applied for data analysis. The data obtained with the individual drugs are subjected to ANOVA followed by multiple comparison tests. For the data obtained with drugs administered in combinations a search for additive or supra-additive activity is systematically assessed using one of the most used approaches in the field: Combination Index method (Chou et al. 1984, with CalcuSyn software from Biosoft, Ferguson, Mo.) or SSI analysis (Lopez-Munoz, 1994) or isobolographic method (Tallarida et al. 1989, 1997).

Compounds or combinations of compounds which modulate by more than 10%, 20% or preferably 50% expression of the target or which produce a statistically significant therapeutic effect in the animal model are selected.

A further object of the invention is a method of producing a drug, the method comprising 1) identifying a drug using the above-described method and 2) producing the drug, preferably in a pharmaceutically acceptable form.

In a preferred embodiment, the pharmaceutical composition is constituted by one or by a combination of approved drugs.

The pharmaceutical composition can comprise conventional excipients according to techniques well known by those skilled in the art and can be administered by different routes, including injection, oral, transdermal, or transmucosal administration.

The pharmaceutical composition is, preferably, used to treat for example, neurologic disorders, psychiatric disorders, cancers, autoimmune diseases, cardiovascular diseases or lipid-metabolism diseases.

In a particular embodiment, the invention is used to produce appropriate pharmaceutical compositions for treating rare, orphan diseases and common diseases with unmet therapeutic need, such as for example, neuropathies, diabetic and drug-induced neuropathies, amyotrophic lateral sclerosis (ALS), stroke, Parkinson's disease, Alzheimer diseases and other dementia, schizophrenia, bipolar disorder, major depression, malaria, tuberculosis.

As discussed above, the invention allows the repositioning of approved drugs for use in novel therapeutic indications. This efficient and biologically relevant method may be used to reposition drugs for any type of disease and it is believed that present application provides a novel strategy to address unmet medical needs.

The following examples are given for purposes of illustration and not by way of limitation.

EXAMPLE 1

Drug Repositioning in Charcot-Marie-Tooth (CMT) Disease 1.1: Disease Selection: The Charcot-Marie-Tooth (CMT) Disease CMT disease is an orphan genetic peripheral poly neuropathy. Affecting approximately 1 in 2,500 individuals, this disease is the most common inherited disorder of the peripheral nervous system. Its onset typically occurs during the first or second decade of life, although it may be detected in infancy. Course of disease is chronic with gradual neuromuscular degeneration. The disease is invalidating with cases of accompanying neurological pain and extreme muscular disability. CMT is one of the best studied genetic pathologies with approximately 30,000 cases in France. Two dozens of genes have been implicated in different forms of this disease but the majority of patients (form CMT1A) harbour a duplication of a chromosome 17 fragment containing an important myelin gene: PMP22. Although monogenic in origin, this pathology manifests clinical heterogeneity due to possible modulator genes.

Several animal models exist for this disease. In one of them (mouse with conditional PMP22 over-expression), the disease is reversed once the expression of PMP22 is normalized. The genes mutated in CMT patients are clustering around tightly connected molecular pathways affecting differentiation Schwann cells or neurons or changing interplay of these cells in peripheral nerves. Blocker of progesterone receptor and ascorbic acid were shown to improve clinical features in CMT animal models.

At least three human clinical trials are under way for large doze vitamin C therapy. Still, it is difficult to expect that this single molecule alone could be very efficient and universal in treating this neuropathy. Finding molecules which will down regulate PMP 22 or molecules which will compensate effect of PMP 22 over-expression will require action on various pathways.

1.2: Building a Dynamic Model of the CMT Disease

CMT1A could be defined as a gene-dosage disease provoked by rather modest, 1.5-fold over expression of a normal PMP22 protein in Schwann cells heterozygous for the duplication (in some rare cases, CMT1A-like phenotype can be also linked to structural mutations in PMP22 protein) (Lupski et al., 1992; Suter et al., 1992; Roa et al., 1993; Thomas et al., 1997; Suter & Scherer, 2003; Nave & Sereda, 2007). This conclusion is supported by a series of clinical and experimental observations. Firstly, the homozygous genomic duplication leads to a more aggravated form of disease, while individuals with a deletion of PMP22 gene (haploinsufficient) develop a milder disease form (HNPP) (Lupski et al., 1991; Chance et al., 1993; Li et al., 2004). Direct evidence that abnormal PMP22 gene dosage is sufficient to cause a CMT1A-like phenotype was provided by transgenic experiments in rodent models with over expression of PMP22 protein (Niemann et al., 1999; Perea et al., 2001; Robaglia-Schlupp et al., 2002; Meyer et al., 2006; Sereda & Nave, 2006). Accordingly, therapeutic interventions decreasing this expression in the transgenic animals ameliorated or slowed the progression of disease phenotype (Sereda et al., 2003; Passage et al., 2004; Meyer zu Horste et al., 2007).

Existing experimental data are indicating that PMP22 protein is not only the structural component of myelin sheaths, but plays also a regulatory role in Schwann cells. The exact mechanism linking abnormal level of the protein to a modification of its functions in a mutant CMT1A glia cell is not completely understood, but some cellular mechanisms explaining its detrimental effects on Schwann cell biology are starting to emerge.

Thus, PMP22 protein interacts with another structural myelin protein P0, and therefore, the altered PMP22/P0 protein ratio might influence the compaction of myelin sheaths (Vallat et al., 1996; D'Urso et al., 1999). As demonstrated by in vitro studies, PMP22 protein is also involved in the regulation of cell spreading in a Rho-dependent manner and thus could affect axonal ensheathment (Brancolini et al., 1999). Moreover, PMP22 forms complexes with α6β4 integrins and could mediate the interaction of Schwann cells with extracellular matrix (Amici et al., 2006; Amici et al., 2007). As the integrin signalling is crucial for the proper development of myelinated axons, modification of the integrin complexes by PMP22 protein in CMT1A Schwann cells could be another cellular mechanism contributing to its pathological actions (Feltri et al., 2002; Berti et al., 2006). Interestingly, demyelinated nerves in CMT1A patients have an abnormal composition of extracellular matrix, pointing that abnormal Schwann cell—extracellular matrix interactions might be tightly connected with a development of disease phenotype (Palumbo et al., 2002). Furthermore, increased level of PMP22 protein can alter the Arf6-regulated plasma membrane endosomal recycling pathway and lead to accumulation of PMP22 in the late endosomes (Chies et al., 2003). It was also demonstrated—both in cultured cells and in vivo in transgenic mice—that overexpressed PMP22 protein forms intracellular ubiquitinated protein aggregates. These findings indicate that over expressed PMP22 protein is misfolded, perturbs intracellular protein sorting and overloads the protein degradation machinery in Schwann cells (Notterpek et al., 1997; Tobler et al., 2002; Fortun et al., 2003; Fortun et al., 2006; Fortun et al., 2007; Khajavi et al., 2007).

In all PMP22 mutant rodents, with increased or decreased PMP22 gene dosage or point mutations affecting the PMP22 gene, increased Schwann cell proliferation and apoptosis were detected demonstrating that altered PMP22 protein signalling is directly involved in the control of cell proliferation and programmed cell death (Sancho et al., 2001; Atanasoski et al., 2002). Finally, mutant PMP22 protein was shown to provoke profound reorganization and the aberrant expression of axonal ion channels (Ulzheimer et al., 2004; Devaux & Scherer, 2005).

Our working hypothesis postulates that a wide range of sub cellular defects induced by over expressed (or mutant) PMP22 protein in Schwann cells,—including, but not limiting to abnormal myelination—could disrupt normal axon-glia interaction necessary for axonal function and survival. This eventually leads to axonal loss, the most clinically relevant pathological hallmark shared by all subforms of CMT disease.

Interestingly, in addition to disrupted Schwann cell biology and axon-glia interactions, the possibility for involvement of the immune system in CMT1 pathology has been demonstrated recently. Namely, a pathological role for CD8+ T cells and macrophages infiltrating demyelinated nerves was confirmed in mice models, where genetic manipulations eliminating either functional T cells or decreasing activation of macrophages reduced substantially myelin pathology (Mäurer et al., 2002; Kobsar et al., 2005). As the possibility of involvement of immune system in demyelination in humans has not been systematically evaluated, these data provide useful guidelines for future clinical studies in CMT patients.

Mining of publicly available data, describing molecular mechanisms and pathological manifestations of the CMT1A disease, allowed us to prioritize a few functional cellular modules—transcriptional regulation of PMP22 gene, PMP22 protein folding/degradation, Schwann cell proliferation and apoptosis, ECM deposition and remodelling, immune response—as targets for CMT-relevant therapeutic interventions. For instance, transcriptional down regulation of PMP22 gene represents a reasonable strategy for therapeutic treatment of CMT1A patients (Sereda et al., 2003; Passage et al., 2004). Experimental data support the evidence that expression of PMP22 protein is regulated by the nuclear progesterone and glucocorticoid receptors and by GABA A and GABA B receptors in rat Schwann cells (Robert et al., 2001; Schumacher et al., 2001; Melcangi et al., 2005). A proof-of-concept experiments with the progesterone receptor antagonist onapristone in a PMP22-transgenic CMT1A rat model showed that antiprogestin treatment decreased expression of PMP22 protein in transgenic rodents and significantly improved clinical symptoms in the drug-treated animals compared with placebo-treated controls (Meyer zu Horste et al., 2007).

1.3: Virtual Screening of Approved Drugs that Target the Dynamic Model of CMT Disease In the case of CMT, the initial building of dynamic model of CMT pathology has been followed by a selection of marketed generic drugs targeting to functional regulation of CMT1A disease-relevant cellular pathways.

In this context, several generic drugs—antagonists/agonists directly regulating activity of progesterone receptors, drugs modulating synthesis of steroids, natural ligands for nuclear and GABA A receptors or drugs affecting conformational state of nuclear receptor complexes and their interaction with ligands were selected as promising candidates for experimental testing (Le Bihan et al., 1998; Magnaghi et al., 2006).

Another feasible way to control transcription of the PMP22 gene is the modulation of intracellular cAMP pool in Schwann cells. It was demonstrated in vitro that exposure of Schwann cell to forskolin increases the expression of PMP22 protein; moreover, a silencer element, which inhibits the transcriptional activity in the absence of cAMP stimulation, was identified in the promoter region of PMP22 gene (Sabéran-Djoneidi et al., 2000). Our model also suggested that pharmaceutical modulation of the receptors expressed in Schwann cells and known to regulate intracellular level of cAMP (ex., adrenergic receptors or muscarinic receptors) might be explored for transcriptional regulation of PMP22 protein (Yasuda et al., 1988; Loreti et al., 2006; Kaya et al., 2007). At the next level, GSK-3β kinase plays a pivotal role in transcriptional control of PMP22 protein through regulation of β-catenin, which serves as a coactivator for glucocorticoid receptor replacing CBP in Schwann cells (Fonte et al., 2005). Phosphorylation status and, respectively, activity of GSK-3β kinase could be modified by several signalling pathways including adrenergic, serotoninergic and muscarinic receptors and AMP-activated protein kinase, for all of which modulator generic drugs exist.

Similar data mining was also performed for selecting generic drugs affecting other cellular processes disturbed by increased expression of PMP22 protein. These processes are located in pathways downstream the function of PMP22 protein and could be tested experimentally directly in animal models of neuropathy.

Overall screening gave 46 drugs to be tested in the next step.

1.4: Testing in Biological Models

In the specific example of CMT, in vitro studies have been conducted to test approved drugs for their potential efficiency to modulate PMP22 expression levels. As a major endpoint for these experiments, we were looking at expression of PMP22 gene and several other myelinisation markers after treatment of Schwann cell cultures with chosen drugs.

This study was conducted on a primary wild-type rat Schwann cell (SC) culture. SC culture model has been used to study the modulation of myelin proteins expression during SC proliferation and differentiation processes (Morgan 1991; Clive 1998; Ogata 2004), the molecular pathways controlling PMP22 expression (Magnaghi 2001, 2004) or the PMP22 transcriptional and post-transcriptional regulations and aggresomes formation ability (Bosse 1999; Ryan 2002; Fortun 2007; Nobbio 2004; Notterpeck 1999; Felitsyn 2007). Altogether, these results encouraged us to choose the simple model in order to screen influence of selected drugs on PMP22 expression.

Thirty seven selected drugs were tested in our cell culture model. Schwann cells were cultivated in a defined medium to promote their differentiation, which is essential for myelin protein expression (Morgan 1991).

After SC incubation with drugs, total RNA is extracted and levels of PMP22 mRNA are quantified using Roche LightCycler® specific fluorescent probes (FRET system). The modulation of PMP22 mRNA levels is normalized in regard to the expression of "housekeeping" gene marker. All cell culture conditions as well as quantifications are done in triplicates.

In the cases when drugs tested individually do not decrease PMP22 mRNA levels, they are combined and tested as combinations assuming that they still could act synergistically.

In conclusion, out of the thirty seven tested drugs, 11 were positive and effectively decreased PMP22 expression, four drugs have shown a trend to statistically significant down regulation of PMP22 expression and 5 drugs were able to up regulate PMP22 expression. These results (Table 1) show that the proposed strategy is particularly efficient and relevant, since about 30% of drugs resulting from the virtual screening turned out to indeed express the relevant biological activity.

TABLE 1

Summary of drug testing

| | |
|---|---|
| Total drugs | 46 |
| Tested in vitro | 37 |
| In vitro down regulated | 11 |
| In vitro trend for down regulation | 4 |
| In vitro up regulated | 5 |

At the next step, we tested some of the compounds in in vivo rat model of CMT1A neuropathy (Sereda et al, 1996). In the behavioural BAR test, the selected compounds demonstrated a significant improvement compared to transgenic placebo animals.

EXAMPLE 2

Drug Repositioning in Alzheimer (AD) Disease

In another example of model building a comprehensive analysis has been performed for Alzheimer disease pathology. Four different pathways have been identified. In silico screening gave 85 distinct candidate molecules, out of which eleven have been tested in cellular model of axon death induced by Abeta amyloid peptide, leading to the selection of candidate drugs. In this process, more than 25% of tested drugs were positive.

BIBLIOGRAPHY

Amici S A, Dunn W A Jr, Murphy A J, Adams N C, Gale N W, Valenzuela D M, Yancopoulos G D, Notterpek L. Peripheral myelin protein 22 is in complex with alpha6beta4 integrin, and its absence alters the Schwann cell basal lamina. J Neurosci. 2006; 26(4):1179-1189.

Amici S A, Dunn W A Jr, Notterpek L. Developmental abnormalities in the nerves of peripheral myelin protein 22-deficient mice. J Neurosci Res. 2007; 85(2): 238-249.

Ashburn T T, Thor K B. Drug repurposing: identify, develop and commercialize new uses for existing drugs. Nat Rev Drug Discov. 2004; 3(8):673-683.

Atanasoski S, Scherer S S, Nave K-A, Suter U. Proliferation of Schwann Cells and Regulation of Cyclin D1 Expression in an Animal Model of Charcot-Marie-Tooth Disease Type 1A. J Neurosci Res. 2002; 67(4):443-449.

Bosse F, Brodbeck J, Müller H W. Post-transcriptional regulation of the peripheral myelin protein gene PMP22/gas3. J Neurosci Res. 1999; 55 (2): 164-177.

Berti C, Nodari A, Wrabetz L, Feltri M L. Role of integrins in peripheral nerves and hereditary neuropathies. Neuromolecular Med. 2006; 8(1-2):191-204.

Brancolini C, Marzinotto S, Edomi P, Agostoni E, Fiorentini C, Müller H W, Schneider C. Rho-dependent regulation of cell spreading by the tetraspan membrane protein Gas3/PMP22. Mol. Biol. Cell 1999; 10: 2441-2459.

Chance P F, Alderson M K, Leppig K A, Lensch M W, Matsunami N, Smith B, Swanson P D, Odelberg S J, Disteche C M, Bird T D. DNA deletion associated with hereditary neuropathy with liability to pressure palsies. Cell 1993; 72(1):143-151.

Chies R, Nobbio L, Edomi P, Schenone A, Schneider C, Brancolini C. Alterations in the Arf6-regulated plasma membrane endosomal recycling pathway in cells overexpressing the tetraspan protein Gas3/PMP22. J Cell Sci. 2003; 116(Pt 6): 987-999.

Chou T-C, Talalay P. Analysis of combined drug effects: a new look at a very old problem. Trends Pharmacol Sci 1983; 4:450-454.

Clive D R, Lopez T J, DeVries G H. Quantitation of changes in P0 mRNA by polymerase chain reaction in primary cultured Schwann cells stimulated by axolemma-enriched fraction. J Neurosci Methods. 1998; 81 (1-2): 25-34.

D'Urso D, Ehrhardt P, Müller H W. Peripheral myelin protein 22 and protein zero: a novel association in peripheral nervous system myelin. J Neurosci. 1999; 19(9):3396-3403.

De Leersnyder H, Bresson J L, de Blois M C, Souberbielle J C, Mogenet A, Delhotal-Landes B, Salefranque F, Munnich A. Beta 1-adrenergic antagonists and melatonin reset the clock and restore sleep in a circadian disorder, Smith-Magenis syndrome. 2003. J Med Genet. 40(1):74-78.

Devaux J J, Scherer S S. Altered ion channels in an animal model of Charcot-Marie-Tooth disease type IA. J Neurosci. 2005; 25(6): 1470-1480.

Felitsyn N, Stacpoole P W, Notterpek L. Dichloroacetate causes reversible demyelination in vitro: potential mechanism for its neuropathic effect. J Neurochem. 2007; 100 (2): 429-436.

Feltri M L, Graus Porta D, Previtali S C, Nodari A, Migliavacca B, Cassetti A, Littlewood-Evans A, Reichardt L F, Messing A, Quattrini A, Mueller U, Wrabetz L. Conditional disruption of β1 integrin in Schwann cells impedes interactions with axons. J. Cell Biol. 2002; 156: 199-209.

Fonte C, Grenier J, Trousson A, Chauchereau A, Lahuna O, Baulieu E E, Schumacher M, Massaad C. Involvement of {beta}-catenin and unusual behavior of CBP and p300 in glucocorticosteroid signaling in Schwann cells. PNAS USA. 2005; 102(40): 14260-14265.

Fortun J, Dunn W A Jr, Joy S, Li J, Notterpek L. Emerging role for autophagy in the removal of aggresomes in Schwann cells. J Neurosci. 2003; 23(33): 10672-10680.

Fortun J, Go J C, Li J, Amici S A, Dunn W A Jr, Notterpek L. Alterations in degradative pathways and protein aggregation in a neuropathy model based on PMP22 overexpression. Neurobiol Dis. 2006; 22(1):153-164.

Fortun J, Verrier J D, Go J C, Madorsky I, Dunn W A, Notterpek L. The formation of peripheral myelin protein 22 aggregates is hindered by the enhancement of autophagy and expression of cytoplasmic chaperones. Neurobiol Dis. 2007; 25(2): 252-265.

ILAR Journal (ISSN 1084-2020) 2002 special issue Experimental Design and Statistics in Biomedical Research Volume 43, Number 4

Kaya F, Belin S, Bourgeois P, Micaleff J, Blin O, Fontes M. Ascorbic acid inhibits PMP22 expression by reducing cAMP levels. Neuromuscul Disord. 2007; 17(3): 248-253.

Khajavi M, Shiga K, Wiszniewski W, He F, Shaw C A, Yan J, Wensel T G, Snipes G J, Lupski J R. Oral curcumin mitigates the clinical and neuropathologic phenotype of the Trembler-J mouse: a potential therapy for inherited neuropathy. Am J Hum Genet. 2007; 81(3): 438-453.

Kobsar I, Hasenpusch-Theil K, Wessig C, Müller H W, Martini R. Evidence for macrophage-mediated myelin disruption in an animal model for Charcot-Marie-Tooth neuropathy type 1A. J Neurosci Res. 2005; 81(6): 857-864.

Le Bihan S, Marsaud V, Mercier-Bodard C, Baulieu E E, Mader S, White J H, Renoir J M. Calcium/calmodulin kinase inhibitors and immunosuppressant macrolides rapamycin and FK506 inhibit progestin- and glucocorticosteroid receptor-mediated transcription in human breast cancer T47D cells. Mol Endocrinol. 1998; 12(7): 986-1001.

Li J, Krajewski K, Lewis R A, Shy M E. Loss-of-function phenotype of hereditary neuropathy with liability to pressure palsies. Muscle Nerve. 2004; 29(2): 205-210.

Lopez-Munoz F J, Villalon C M, Terron J A, Salazar L A. Analgesic interactions produced by combinations of dipyrone and morphine in the rat. Proc West Pharmacol Soc. 1994; 37: 17-19.

Loreti S, Vilaró M T, Visentin S, Rees H, Levey A I, Tata A M. Rat Schwann cells express M1-M4 muscarinic receptor subtypes. J Neurosci Res. 2006; 84(1): 97-105.

Lupski J R, de Oca-Luna R M, Slaugenhaupt S, Pentao L, Guzzetta V, Trask B J, Saucedo-Cardenas O, Barker D F, Killian J M, Garcia C A, Chakravarti A, Patel P I. DNA duplication associated with Charcot-Marie-Tooth disease type 1A. Cell. 1991; 66(2):219-232.

Lupski J R, Wise C A, Kuwano A, Pentao L, Parke J T, Glaze D G, Ledbetter D H, Greenberg F, Patel P I. Gene dosage is a mechanism for Charcot-Marie-Tooth disease type 1A. Nat Genet. 1992;1(1): 29-33.

Magnaghi V, Ballabio M, Cavarretta I T, Froestl W, Lambert J J, Zucchi I, Melcangi R C. GABAB receptors in Schwann cells influence proliferation and myelin protein expression. Eur J Neurosci. 2004; 19 (10): 2641-2649.

Magnaghi V, Ballabio M, Consoli A, Lambert J J, Roglio I, Melcangi R C. GABA receptor-mediated effects in the peripheral nervous system: A cross-interaction with neuroactive steroids. J Mol Neurosci. 2006; 28(1):89-102.

Magnaghi V, Cavarretta I, Galbiati M, Martini L, Melcangi R C. Neuroactive steroids and peripheral myelin proteins. Brain Res Brain Res Rev. 2001; 37 (1-3): 360-371.

Mäurer M, Kobsar I, Berghoff M, Schmid C D, Carenini S, Martini R. Role of immune cells in animal models for inherited neuropathies: facts and visions. J Anat. 2002; 200(4): 405-414.

Melcangi R C, Cavarretta I T, Ballabio M, Leonelli E, Schenone A, Azcoitia I, Miguel Garcia-Segura L, Magnaghi V. Peripheral nerves: a target for the action of neuroactive steroids. Brain Res Rev. 2005; 48(2): 328-338.

Mercuri E, Bertini E, Messina S, Pelliccioni M, D'Amico A, Colitto F, Mirabella M, Tiziano F D, Vitali T, Angelozzi C, Kinali M, Main M, Brahe C. Pilot trial of phenylbutyrate in spinal muscular atrophy. Neuromuscul Disord. 2004; 14(2): 130-135.

Meyer zu Horste G, Prukop T, Liebetanz D, Mobius W, Nave K A, Sereda M W. Antiprogesterone therapy uncouples axonal loss from demyelination in a transgenic rat model of CMT1A neuropathy. Ann Neurol. 2007; 61 (1): 61-72.

Meyer Zu Horste G., Nave K-A. Animal models of inherited neuropathies. Curr. Opin. Neurol. 2006; 19(5): 464-473.

Morgan L, Jessen K R, Mirsky R. The effects of cAMP on differentiation of cultured Schwann cells: progression from an early phenotype (04+) to a myelin phenotype (P0+, GFAP-, N-CAM-, NGF-receptor-) depends on growth inhibition. J Cell Biol. 1991; 112 (3): 457-467.

Nave K A, Sereda M W, Ehrenreich H. Mechanisms of disease: inherited demyelinating neuropathies—from basic to clinical research. Nat Clin Pract Neurol. 2007; 3(8): 453-464.

Niemann S., Sereda M. W., Rossner M., Stewart H., Suter U., Meinck H. M., Griffiths I. R., Nave K-A. The "CMT rat": peripheral neuropathy and dysmyelination caused by transgenic overexpression of PMP22. Ann. N.-Y. Acad. Sci. 1999; 883:254-261.

Nobbio L, Vigo T, Abbruzzese M, Levi G, Brancolini C, Mantero S, Grandis M, Benedetti L, Mancardi G, Schenone A. Impairment of PMP22 transgenic Schwann cells differentiation in culture: implications for Charcot-Marie-Tooth type 1A disease. Neurobiol Dis. 2004; 16 (1): 263-273.

Notterpek L, Shooter E M, Snipes G J. Upregulation of the endosomal-lysosomal pathway in the trembler-J neuropathy. J Neurosci. 1997;17(11): 4190-4200.

Notterpek L, Snipes G J, Shooter E M. Temporal expression pattern of peripheral myelin protein 22 during in vivo and in vitro myelination. Glia 1999; 25 (4): 358-369.

Ogata T, Iijima S, Hoshikawa S, Miura T, Yamamoto S, Oda H, Nakamura K, Tanaka S. Opposing extracellular signal-regulated kinase and Akt pathways control Schwann cell myelination. J Neurosci. 2004; 24 (30): 6724-6732.

Palumbo C, Massa R, Panico M B, Di Muzio A, Sinibaldi P, Bernardi G, Modesti A. Peripheral nerve extracellular matrix remodeling in Charcot-Marie-Tooth type I disease. Acta Neuropathol (Berl). 2002; 104(3): 287-296.

Passage E, Norreel J C, Noack-Fraissignes P, Sanguedolce V, Pizant J, Thirion X, Robaglia-Schlupp A, Pellissier J F, Fontes M. Ascorbic acid treatment corrects the phenotype of a mouse model of Charcot-Marie-Tooth disease. Nature Med. 2004; 10(4): 396-401.

Perea J, Robertson A, Tolmachova T, Muddle J, King R H, Ponsford S, Thomas P K, Huxley C. Induced myelination and demyelination in a conditional mouse model of Charcot-Marie-Tooth disease type 1A. Hum Mol Genet. 2001; 10(10): 1007-1018.

Roa B B, Garcia C A, Suter U, Kulpa D A, Wise C A, Mueller J, Welcher A A, Snipes G J, Shooter E M, Patel P I, Lupski J R. Charcot-Marie-Tooth disease type 1A. Association with a spontaneous point mutation in the PMP22 gene. N Engl J Med. 1993; 329(2): 96-101.

Robaglia-Schlupp A, Pizant J, Norreel J C, Passage E, Saberan-Djoneidi D, Ansaldi J L, Vinay L, Figarella-Branger D, Levy N, Clarac F, Cau P, Pellissier J F, Fontes M. PMP22 overexpression causes dysmyelination in mice. Brain 2002; 125(Pt 10): 2213-2221.

Robert F, Guennoun R, Désarnaud F, Do-Thi A, Benmessahel Y, Baulieu E E, Schumacher M. Synthesis of progesterone in Schwann cells: regulation by sensory neurons. Eur J Neurosci. 2001; 13(5): 916-924.

Rustin P, von Kleist-Retzow J C, Chantrel-Groussard K, Sidi D, Munnich A, Rötig A. Effect of idebenone on cardiomyopathy in Friedreich's ataxia: a preliminary study. Lancet 1999; 354 (9177): 477-479.

Ryan M C, Shooter E M, Notterpek L. Aggresome formation in neuropathy models based on peripheral myelin protein 22 mutations. Neurobiol Dis. 2002; 10 (2): 109-118.

Sabéran-Djoneidi D, Sanguedolce V, Assouline Z, Lévy N, Passage E, Fontés M. Molecular dissection of the Schwann cell specific promoter of the PMP22 gene. Gene 2000; 248 (1-2): 223-231.

Sancho S, Young P, Suter U. Regulation of Schwann cell proliferation and apoptosis in PMP22-deficient mice and mouse models of Charcot-Marie-Tooth disease type 1A. Brain 2001; 124(Pt 11): 2177-2187.

Schumacher M, Guennoun R, Mercier G, Désarnaud F, Lacor P, Bénavides J, Ferzaz B, Robert F, Baulieu E E. Progesterone synthesis and myelin formation in peripheral nerves. Brain Res Rev. 2001; 37(1-3): 343-359.

Schworer C M, Masker K K, Wood G C, Carey D J. Microarray analysis of gene expression in proliferating Schwann cells: synergistic response of a specific subset of genes to the mitogenic action of heregulin plus forskolin. J Neurosci Res. 2003; 13 (4): 456-464.

Sereda M W, Griffiths I, Puhlhofer A, et al. A transgenic rat model of Charcot-Marie-Tooth disease. Neuron 1996; 16: 1049-1060.

Sereda M W, Meyer zu Horste G, Suter U, et al. Therapeutic administration of progesterone antagonist in a model of Charcot-Marie-Tooth disease (CMT-1A). Nat Med 2003; 9: 1533-1537.

Sereda M W, Nave K A. Animal models of Charcot-Marie-Tooth disease type 1A (CMT1A). Neuromol Med 2006; 8: 205-215.

Shy M E. Charcot-Marie-Tooth disease: an update. Curr Opin Neurol. 2004; 17 (5): 579-585.

Suter U, Welcher A A, Ozcelik T, Snipes G J, Kosaras B, Francke U, Billings-Gagliardi S, Sidman R L, Shooter E M. Trembler mouse carries a point mutation in a myelin gene. Nature. 1992; 356(6366): 241-244.

Suter U, Scherer S S. Disease mechanisms in inherited neuropathies. Nat. Rev. Neurosci. 2003; 4: 714-726.

Tallarida R J, Porreca F, Cowan A. Statistical analysis of drug-drug and site-site interactions with isobolograms. Life Sci 1989; 45: 947-961.

Tallarida R J, Stone D J, Raffa B B. Efficient designs for studying synergistic drug combinations. Life Sci 1997; 61: 417-425.

Thomas P K, Marques W Jr, Davis M B, Sweeney M G, King R H, Bradley J L, Muddle J R, Tyson J, Malcolm S, Harding A E. The phenotypic manifestations of chromosome 17p11.2 duplication. Brain 1997; 120 (Pt 3): 465-478.

Tobler A R, Liu N, Mueller L, Shooter E M. Differential aggregation of the Trembler and Trembler J mutants of peripheral myelin protein 22. PNAS USA. 2002; 99(1):483-488.

Ulzheimer J C, Peles E, Levinson S R, Martini R. Altered expression of ion channel isoforms at the node of Ranvier in P0-deficient myelin mutants. Mol Cell Neurosci. 2004; 25(1): 83-94.

Vallat J M, Sindou P, Preux P M, Tabaraud F, Milor A M, Couratier P, LeGuern E, Brice A. Ultrastructural PMP22 expression in inherited demyelinating neuropathies. Ann Neurol. 1996; 39(6): 813-817.

Vigo T, Nobbio L, Hummelen P V, Abbruzzese M, Mancardi G, Verpoorten N, Verhoeven K, Sereda M W, Nave K A, Timmerman V, Schenone A. Experimental Charcot-Marie-Tooth type 1A: a cDNA microarrays analysis. Mol Cell Neurosci. 2005; 28 (4):703-714.

Yasuda T, Sobue G, Mitsuma T, Takahashi A. Peptidergic and adrenergic regulation of the intracellular 3',5'-cyclic adenosine monophosphate content in cultured rat Schwann cells. J Neurol Sci. 1988; 88(1-3): 315-325.

The invention claimed is:

1. A method of identifying drug candidates for the combinatorial treatment of a selected disease, the method comprising the steps of:
   a) building a dynamic model of a selected disease in silico comprising:
      (i) performing multivariate genetic, proteomic and metabolomics statistical analysis of groups of genes and establishing disease-associated pathways involved in disease genesis and progression, said disease-associated pathways being targets for drug development;
      (ii) testing data of (i) on whole pathway association and validating results in another data set; and
      (iii) organizing emerging pathways in a hierarchical model and defining the most relevant mechanisms or cell targets by which the disease may be corrected;
   b) in silico screening of drugs approved for other diseases that target pathways implicated in the model and selecting at least two drugs which interact concurrently with several different target pathways implicated in the dynamic model;

c) testing drugs selected in b) in an in vitro and/or in vivo biological model of the selected disease to select biologically active drugs; and d) identifying from drugs selected in c) a drug combination having a synergistic effect for the treatment of said selected disease, at doses lower than those approved for said other diseases.

2. The method of claim 1, wherein the disease is selected from neurologic disorders, psychiatric disorders, cancers, autoimmune diseases, cardiovascular diseases, lipid-metabolism diseases, and neuropathies.

3. The method of claim 2, wherein the disease is Charcot-Marie-Tooth disease, Parkinson's disease or Alzheimer's disease.

4. The method of claim 1, wherein drugs selected in step b) are tested in an in vitro model of the disease, wherein drugs which affect expression of a target by more than 10% or disease progression in the model are selected as candidate drugs for a combination of drugs.

5. The method of claim 1, wherein drugs selected in step b) are tested, in an in vivo model of the disease, wherein drugs which affect expression of a target by more than 10% or disease progression in the model are selected as candidate drugs for a combination of drugs.

6. The method of claim 1, wherein drugs selected in step b) are tested, in both an in vitro and an in vivo model of the disease, wherein drugs which affect expression of a target by more than 10% or disease progression in the model are selected as candidate drugs for a combination of drugs.

7. The method of claim 1, wherein said disease is Charcot-Marie-Tooth disease and about 30% of the drugs identified in step b) have biological activity in vitro.

8. A method of producing a candidate combination of drugs for treating a selected disease, the method comprising:

1) identifying a combination of drugs by:

a) building a dynamic model of the selected disease in silico, comprising;

(i) performing multivariate genetic, proteomic and metabolomics statistical analysis of groups of genes and establishing disease-associated pathways involved in disease genesis and progression, said disease-associated pathways being targets for drug development;

(ii) testing data of (i) on whole pathway association and validating results in another data set; and (iii) organizing emerging pathways in a hierarchical model and defining the most relevant mechanisms or cell targets by which the disease may be corrected;

b) screening of drugs approved for other diseases that target pathways implicated in the model in silico and selecting at least two drugs which interact concurrently with several different target pathways implicated in the dynamic model;

c) testing drugs selected in b) in an in vitro and/or in vivo biological model of the disease, to select biologically active drug combinations; and d) identifying from drugs selected in c) a drug combination having a synergistic effect for the treatment of said selected disease at doses lower than those approved for said other diseases; and 2) formulating the combination(s) of drugs having a synergistic effect for the treatment of said selected disease at doses lower than those approved for said other diseases in a pharmaceutically acceptable form.

* * * * *

UNITED STATES PATENT AND TRADEMARK OFFICE
CERTIFICATE OF CORRECTION

PATENT NO. : 8,571,804 B2  
APPLICATION NO. : 12/744363  
DATED : October 29, 2013  
INVENTOR(S) : Daniel Cohen et al.

Page 1 of 1

It is certified that error appears in the above-identified patent and that said Letters Patent is hereby corrected as shown below:

In The Specification

Column 2,
Line 38, "200000" should read --200,000--.

Column 4,
Line 40, "university" should read --University--.

Column 5,
Line 20, "comprises" should read --comprise--.

Column 6,
Lines 45-46, "Two dozens of genes" should read --Two dozen genes--.
Lines 61-62, "large doze" should read --large dose--.

Signed and Sealed this
Thirteenth Day of January, 2015

Michelle K. Lee
*Deputy Director of the United States Patent and Trademark Office*